United States Patent
Andre et al.

(10) Patent No.: US 10,988,423 B2
(45) Date of Patent: *Apr. 27, 2021

(54) GAS-PHASE CATALYTIC FLUORINATION WITH CHROMIUM CATALYSTS

(71) Applicant: Arkema France, Colombes (FR)

(72) Inventors: David Andre, Brignais (FR);
Dominique Deur-Bert, Charly (FR);
Dominique Garrait, Charly (FR);
Anne Pigamo, Francheville (FR);
Laurent Wendlinger, Soucieu en Jarrest (FR)

(73) Assignee: Arkema France, Colombes (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/742,518

(22) Filed: Jan. 14, 2020

(65) Prior Publication Data

US 2020/0148612 A1  May 14, 2020

Related U.S. Application Data

(63) Continuation of application No. 16/060,037, filed as application No. PCT/FR2016/053236 on Dec. 7, 2016, now Pat. No. 10,577,294.

(30) Foreign Application Priority Data

Dec. 14, 2015 (FR) ..................................... 1562276

(51) Int. Cl.
| | | |
|---|---|---|
| C07C 17/20 | (2006.01) | |
| B01J 38/46 | (2006.01) | |
| B01J 23/92 | (2006.01) | |
| B01J 37/14 | (2006.01) | |
| B01J 37/18 | (2006.01) | |
| B01J 38/10 | (2006.01) | |
| B01J 38/12 | (2006.01) | |
| B01J 27/32 | (2006.01) | |
| B01J 37/12 | (2006.01) | |
| B01J 37/16 | (2006.01) | |
| B01J 27/132 | (2006.01) | |
| C07C 17/21 | (2006.01) | |
| B01J 23/26 | (2006.01) | |
| B01J 37/26 | (2006.01) | |
| B01J 38/42 | (2006.01) | |
| B01J 38/04 | (2006.01) | |
| B01J 37/24 | (2006.01) | |
| C07C 17/087 | (2006.01) | |
| C07C 19/08 | (2006.01) | |

(52) U.S. Cl.
CPC ............ *C07C 17/206* (2013.01); *B01J 23/26* (2013.01); *B01J 23/92* (2013.01); *B01J 27/132* (2013.01); *B01J 27/32* (2013.01); *B01J 37/12* (2013.01); *B01J 37/14* (2013.01); *B01J 37/16* (2013.01); *B01J 37/18* (2013.01); *B01J 37/24* (2013.01); *B01J 37/26* (2013.01); *B01J 38/04* (2013.01); *B01J 38/10* (2013.01); *B01J 38/12* (2013.01); *B01J 38/42* (2013.01); *B01J 38/46* (2013.01); *C07C 17/087* (2013.01); *C07C 17/21* (2013.01); *B01J 2523/67* (2013.01); *C07C 19/08* (2013.01); *Y02P 20/584* (2015.11)

(58) Field of Classification Search
CPC ..... C07C 17/087; C07C 17/206; C07C 17/25; C07C 17/42; C07C 21/18; C07C 19/10; B01J 37/26; B01J 23/866; B01J 23/92; B01J 38/18; B01J 38/12
See application file for complete search history.

(56) References Cited

U.S. PATENT DOCUMENTS

| | | |
|---|---|---|
| 5,817,895 A | 10/1998 | Cuzzato |
| 2009/0240090 A1 | 9/2009 | Merkel et al. |
| 2011/0155942 A1 | 6/2011 | Pigamo |

FOREIGN PATENT DOCUMENTS

| | | |
|---|---|---|
| EP | 0806242 A1 | 11/1997 |
| EP | 0939071 A1 | 9/1999 |
| JP | H0592141 A | 4/1993 |
| WO | 2007079431 A2 | 7/2007 |
| WO | 2008002500 A1 | 1/2008 |
| WO | 2008040969 A2 | 4/2008 |

(Continued)

OTHER PUBLICATIONS

ISA/EP, International Search Report and Written Opinion for PCT Patent Application No. PCT/FR2016/053236, dated Mar. 7, 2017, 14 pages.

(Continued)

*Primary Examiner* — Jafar F Parsa
(74) *Attorney, Agent, or Firm* — NK Patent Law

(57) ABSTRACT

A process for the fluorination of a chlorinated C3 alkane or alkene compound having at least one chlorine atom into a fluorinated C3 alkane or alkene compound having at least one fluorine atom includes the following steps: a) contacting, in a reactor, the chlorinated compound with hydrogen fluoride in gas phase in the presence of a fluorination catalyst to produce a fluorinated compound, and b) regenerating the fluorination catalyst used in step a). The step (b) of regenerating the fluorination catalyst comprises (c) the treatment of said fluorination catalyst with an oxidizing agent-containing gas flow to form an oxidized fluorination catalyst, and (d) the treatment of the oxidized fluorination catalyst obtained in step (c) with a gaseous mixture comprising a reducing agent and an inert gas. The catalyst regenerated in step b) is reused in step a) and the reducing agent is selected from $C_1$-$C_{10}$ hydrohalocarbons.

17 Claims, No Drawings

(56) References Cited

FOREIGN PATENT DOCUMENTS

| WO | 2008054781 A1 | 5/2008 |
| WO | 2009015317 A1 | 1/2009 |
| WO | 2010123154 A2 | 10/2010 |
| WO | 2012098421 A1 | 7/2012 |
| WO | 2012098422 A1 | 7/2012 |
| WO | 2013055722 A1 | 4/2013 |
| WO | 2013055726 A1 | 4/2013 |
| WO | 2014120493 A1 | 8/2014 |

OTHER PUBLICATIONS

Teinz, Katharina, et al., "Applied Catalysis B: Environmental: Catalytic formation of 2,3,3,3-tetrafluoropropene from 2-chloro-3,3,3-trifluoropropene at fluorinated chromia: A study of reaction pathways", Elsevier, vol. 165, Apr. 2015, 10 pages.

GAS-PHASE CATALYTIC FLUORINATION WITH CHROMIUM CATALYSTS

CROSS REFERENCE TO RELATED APPLICATIONS

This application is a continuation of U.S. application Ser. No. 16/060,037, filed Jun. 7, 2018, which is a U.S. National Stage application of International Application No. PCT/FR2016/053236, filed Dec. 7, 2016, which claims the benefit of French Patent Application No. 1562276, filed Dec. 14, 2015.

FIELD OF THE INVENTION

The present invention relates to a catalytic gas phase fluorination process. Preferably, the present invention relates to a catalytic gas phase process for the fluorination of a chlorinated compound into a fluorinated compound in the presence of hydrogen fluoride. In particular, the present invention relates to a process wherein the fluorination reaction is carried out in the presence of a catalyst which is regenerated.

BACKGROUND OF THE PRESENT INVENTION

The Montreal Protocol for the protection of the ozone layer mandated the phase out of the use of chlorofluorocarbons (CFCs). Materials friendlier to the ozone layer, such as hydrofluorocarbons (HFCs), e.g. HFC-134a, replaced chlorofluorocarbons. The latter compounds have proven to be greenhouse gases, causing global warming. They were regulated by the Kyoto Protocol on Climate Change. With the continued concern over global climate change there is an increasing need to develop technologies to replace those with high ozone depletion potential (ODP) and high global warming potential (GWP). Though hydrofluorocarbons (HFCs), being non-ozone depleting compounds, have been identified as alternatives to chlorofluorocarbons (CFCs) and hydrochlorofluorocarbons (HCFCs) as solvents, cleaning agents and heat transfer fluids, they still tend to have significant GWP. Hydrofluoroolefins (HFOs) have been identified as potential alternatives with zero ODP and low GWP.

Hence, numerous documents describe processes for making such HFOs, including HFO-1234yf.

For example, WO 2007/079431 discloses processes for the production of fluorinated olefins, including hydrofluoropropenes. The processes which are broadly described as a single reaction or two or more reactions involve fluorination of a compound of the formula $C(X)_m CCl(Y)_n C(X)_m$, to at least one compound of formula $CF_3CF=CHZ$, where each X, Y and Z is independently H, F, Cl, I or Br and each m is independently 1, 2 or 3 and n is 0 or 1. HFO-1234yf is prepared by fluorinating HFCO-1233xf into 1,1,1,2-tetrafluoro-2-chloropropane (HCFC-244bb), followed by dehydrochlorination. HFCO-1233xf is prepared by fluorination of the corresponding chlorinated precursor ($CCl_2=CClCH_2Cl$).

EP-A-939071 discloses, among many possibilities, gas-phase fluorination of a halogenated propene (according to a very long list) into a fluorinated propene (including in the list HFO-1234yf).

WO 2008/054781 discloses a variety of processes for producing a variety of fluoropropanes and halofluoropropenes by reacting halopropanes or halopropenes with HF, optionally in the presence of a catalyst. It discloses a process for making HFO-1234yf by reacting 2,3-dichloro-1,1,1-trifluoropropane (HCFC-243db) in the presence of HF, on a catalyst, especially Cr/Co (98/2). Reaction products comprise HFO-1234yf and HFCO-1233xf, the latter being the main product; other products are 1-chloro-3,3,3-trifluoro-1-propene (HFCO-1233zd) as well as 1,1,1,2,2-pentafluoropropane (HFC-245cb) and 1,3,3,3-tetrafluoro-1-propene (HFO-1234ze).

WO 2008/002500 discloses a process for making a mixture of HFO-1234yf and HFO-1234ze by catalytic conversion of 1,1,1,2,3-pentafluoropropane (HFC-245eb) on a dehydrofluorination catalyst.

WO 2008/040969 discloses a process comprising dehydrochlorination of HCFC-243db into HFCO-1233 (xf as well as zd), followed by a reaction involving formation of 1,1,1,2-tetrafluoro-2-chloropropane (HCFC-244bb) and later formation of the desired HFO-1234yf through dehydrochlorination. Example 1 of said document discloses a gas phase reaction at atmospheric pressure of HCFC-243db with HF on a Zn/chromium dioxide catalyst, whereby HFO-1234yf and HFCO-1233xf are formed, together with a small amount of HFC-245cb.

WO 2009/015317 discloses the reaction of a chlorinated compound which can be 1,1,2,3-tetrachloro-1-propene (HCO-1230xa), 1,1,1,2,3-pentachloropropane (HCC-240db) or 2,3,3,3-tetrachloro-1-propene (HCO-1230xf) with HF, in gas phase, on a catalyst and in the presence of at least one stabilizer. This process makes it possible to obtain 2-chloro-3,3,3-trifluoro-1-propene (HFCO-1233 xf).

US 2009/0240090 discloses a process for making 2,3,3,3-tetrafluoro-1-propene (HFO-1234yf) starting from a compound of formula (I) $CX_2=CClCH_2X$, or of formula (II) $CX_3CCl=CH_2$ or of formula (III) $CX_3CHClCH_2X$ with X=F, Cl, Br, I. The process comprises three steps, which can be followed by purification. The process includes recycling steps allowing higher conversions and yields to be obtained.

WO 2010/123154 is directed to a process for producing HFO-1234yf starting from HFCO-1233xf, by reacting it with HF in the presence of oxygen and a catalyst comprising chromium oxide or fluorinated chromium oxide.

WO2012/098421 and WO2012/098422 relate to processes for the catalytic gas phase fluorination of 2-chloro-3,3,3-trifluoro-1-propene or of 1,1,1,2,3-pentachloropropane to produce 2,2,2,3-tetrafluoropropene. The regeneration of the catalyst is carried out in the presence of an oxidizing agent.

There is still a need to provide an improved process for making fluoroolefins such as HFO-1234yf, having in particular an improved conversion rate and/or an improved selectivity and/or which is effective over a longer period of time.

SUMMARY OF THE INVENTION

In a first aspect, the present invention provides a process for the fluorination of a chlorinated C3 alkane or alkene compound having at least one chlorine atom into a fluorinated C3 alkane or alkene compound having at least one fluorine atom comprising the following steps:
 (a) contacting, in a reactor, the chlorinated compound with hydrogen fluoride in gas phase in the presence of a fluorination catalyst to produce the fluorinated compound, and
 (b) regenerating the fluorination catalyst used in step a), wherein the step (b) of regenerating the fluorination catalyst comprises (c) the treatment of said fluorination catalyst with an oxidizing agent-containing gas flow to form an oxidized fluorination catalyst, and (d) the treatment of the oxidized fluorination catalyst obtained in step (c) with a gaseous mixture comprising a reducing agent and an inert gas; the catalyst regenerated in step b) being reused in step a) and the reducing agent being selected from the group consisting of hydrogen, carbon monoxide, nitrogen monoxide, formaldehyde, $C_1$-$C_6$ alkanes and $C_1$-$C_{10}$ hydrohalocarbons.

The present process allows the improvement of the conversion or of the selectivity of the reaction. Indeed, it has been observed that by subjecting the fluorination catalyst to a regeneration step as called for in the invention, the presence of by-products is limited or avoided, in particular when the fluorination catalyst so-regenerated is used in step a).

In another embodiment, the inert gas is selected from nitrogen, helium, argon or mixtures thereof. Preferably, when the reducing agent is a $C_1$-$C_{10}$ hydrohalocarbon, the gaseous mixture comprises HF.

In a preferred embodiment, the reducing agent may be a gaseous reducing agent. Preferably, the reducing agent may be selected from the group consisting of hydrogen or $C_1$-$C_{10}$ hydrohalocarbons, in particular the reducing agent is selected from the group consisting of hydrogen and $C_2$-$C_6$ hydrohalocarbons.

In a preferred embodiment, the gaseous mixture of step (d) comprises from 1 to 10% by volume of reducing agent, preferably from 2 to 9% by volume, more preferably from 3 to 7% by volume, based on the total volume of the gaseous mixture.

Preferably, the gaseous mixture from step (d) comprises hydrogen and nitrogen or argon, preferably consists of hydrogen and nitrogen; or the gaseous mixture from step (d) comprises a $C_2$-$C_6$ hydrohalocarbon, nitrogen or argon, and HF, preferably the gaseous mixture from step (d) comprises a C3 hydrohalocarbon, nitrogen and HF.

Preferably, step (d) is carried out at a temperature ranging from 100° C. to 450° C., with a contact time of from 1 to 100 s, preferably of from 1 to 75 s, more preferably of from 5 to 50 s, for a time greater than 1 hour, preferably from 1 to 50 hours, in particular from 4 to 25 hours.

In a preferred embodiment, the chlorinated compound may be selected from the group consisting of 2-chloro-3,3,3-trifluoro-1-propene (HFCO-1233 xf), 1,1,1,2,3-pentachloropropane (HCC-240db), 1,1,2,2,3-pentachloropropane (HCC-240aa), 2,3-dichloro-1,1,1-trifluoropropane (HCFC-243db), 1,1,2,3-tetrachloro-1-propene (HCO-1230xa), 2,3,3,3-tetrachloro-1-propene (HCO-1230xf), 2-chloro-1,1,1,2-tetrafluoropropane (HCFC-244bb), 1,1,1,3,3-pentachloropropane (HCC-240fa), 1,1,3,3-tetrachloropropene (HCO-1230za), 1,3,3,3-tetrachloropropene (HCO-1230zd), 1-chloro-3,3,3-trifluoropropene (HCFO-1233zd), 1,1,1,3-tetrachloropropane (HCC-250fb), 1,1,3-trichloropropene (HCO-1240za), 3,3,3-trichloropropene (HCO-1240zf); more preferably, the chlorinated compound may be selected from the group consisting of 2-chloro-3,3,3-trifluoro-1-propene (HFCO-1233xf), 1,1,1,2,3-pentachloropropane (HCC-240db), 1,1,2,2,3-pentachloropropane (HCC-240aa), 2,3-dichloro-1,1,1-trifluoropropane (HCFC-243db), 1,1,2,3-tetrachloro-1-propene (HCO-1230xa), 2,3,3,3-tetrachloro-1-propene (HCO-1230xf), 2-chloro-1,1,1,2-tetrafluoropropane (HCFC-244bb).

In a preferred embodiment, the fluorinated compound is 2,3,3,3-tetrafluoro-1-propene (HFO-1234ye, 2-chloro-1,1,1,2-tetrafluoropropane (HCFC-244bb), 1,1,1,2,2-pentafluoropropane (HFC-245cb), 1,1,1,3,3-pentafluoropropane (HFC-245 fa), 1,1,1,3-tetrafluoro-3-chloropropane (HCFC-244fa), 1-chloro-3,3,3-trifluoropropene (HCFO-1233 zd), 1,3,3,3-tetrafluoropropene (HFO-1234ze), 3,3,3-trifluoropropene (HFO-1243zf) and 2-chloro-3,3,3-trifluoro-1-propene (HFCO-1233xf).

Preferably, the chlorinated compound and the fluorinated compound are different. For example, when 2-chloro-3,3,3-trifluoro-1-propene (HFCO-1233xf) is the chlorinated compound, then the fluorinated compound obtained in step a) is different from 2-chloro-3,3,3-trifluoro-1-propene (HFCO-1233 xf). In addition, when 2-chloro-3,3,3-trifluoro-1-propene (HFCO-1233xf) is the fluorinated compound obtained in step a), the chlorinated compound used as starting material in step a) is different from 2-chloro-3,3,3-trifluoro-1-propene (HFCO-1233xf).

In a preferred embodiment, the fluorination of the chlorinated compound into a fluorinated compound is:

2-chloro-3,3,3-trifluoro-1-propene (HFCO-1233xf) to 2,3,3,3-tetrafluoro-1-propene (HFO-1234yf);
1,1,1,2,3-pentachloropropane (HCC-240db) to 2,3,3,3-tetrafluoro-1-propene (HFO-1234ye;
1,1,2,2,3-pentachloropropane (HCC-240aa) to 2,3,3,3-tetrafluoro-1-propene (HFO-1234ye;
2,3-dichloro-1,1,1-trifluoropropane (HCFC-243db) to 2,3,3,3-tetrafluoro-1-propene (HFO-1234yf);
1,1,2,3-tetrachloro-1-propene (HCO-1230xa) to 2,3,3,3-tetrafluoro-1-propene (HFO-1234ye;
2,3,3,3-tetrachloro-1-propene (HCO-1230xf) to 2,3,3,3-tetrafluoro-1-propene (HFO-1234ye;
1,1,1,2,3-pentachloropropane (HCC-240db) to 2-chloro-3,3,3-trifluoro-1-propene (HFCO-1233xf);
1,1,2,2,3-pentachloropropane (HCC-240aa) to 2-chloro-3,3,3-trifluoro-1-propene (HFCO-1233xf);
2,3-dichloro-1,1,1-trifluoropropane (HCFC-243db) to 2-chloro-3,3,3-trifluoro-1-propene (HFCO-1233xf);
1,1,2,3-tetrachloro-1-propene (HCO-1230xa) to 2-chloro-3,3,3-trifluoro-1-propene (HFCO-1233xf);
2,3,3,3-tetrachloro-1-propene (HCO-1230xf) to 2-chloro-3,3,3-trifluoro-1-propene (HFCO-1233xf);
2-chloro-3,3,3-trifluoro-1-propene (HFCO-1233 xf) to 2-chloro-1,1,1,2-tetrafluoropropane (HCFC-244bb);
1,1,1,2,3-pentachloropropane (HCC-240db) to 2-chloro-1,1,1,2-tetrafluoropropane (HCFC-244bb);
1,1,2,2,3-pentachloropropane (HCC-240aa) to 2-chloro-1,1,1,2-tetrafluoropropane (HCFC-244bb);
2,3-dichloro-1,1,1-trifluoropropane (HCFC-243 db) to 2-chloro-1,1,1,2-tetrafluoropropane (HCFC-244bb);
1,1,2,3-tetrachloro-1-propene (HCO-1230xa) to 2-chloro-1,1,1,2-tetrafluoropropane (HCFC-244bb);
2,3,3,3-tetrachloro-1-propene (HCO-1230xf) to 2-chloro-1,1,1,2-tetrafluoropropane (HCFC-244bb);
1,1,1,2,3-pentachloropropane (HCC-240db) to 1,1,1,2,2-pentafluoropropane (HFC-245cb);
1,1,2,2,3-pentachloropropane (HCC-240aa) to 1,1,1,2,2-pentafluoropropane (HFC-245cb);
2,3-dichloro-1,1,1-trifluoropropane (HCFC-243db) to 1,1,1,2,2-pentafluoropropane (HFC-245cb);
1,1,2,3-tetrachloro-1-propene (HCO-1230xa) to 1,1,1,2,2-pentafluoropropane (HFC-245cb);
2,3,3,3-tetrachloro-1-propene (HCO-1230xf) to 1,1,1,2,2-pentafluoropropane (HFC-245cb).

In a preferred embodiment, the fluorination catalyst may comprise chromium oxyfluoride, chromium oxides, chromium halides and mixtures thereof. Chromium halides refer to chromium fluorides and/or chromium chlorides.

In a preferred embodiment, the fluorination catalyst may also contain one or more co-catalysts comprising a salt of a transition metal selected from the group consisting of Co, Zn, Mn, Mg, V, Mo, Te, Nb, Sb, Ta, Ni; or a phosphorous salt.

In a preferred embodiment, the process comprises an activation step carried out before step (a) which comprises a first step of contacting the fluorination catalyst with a gas flow containing an oxidizing agent selected from oxygen, air, chlorine or a mixture of oxygen and nitrogen.

In a preferred embodiment, the activation step may also comprise a second step, subsequent to the first step, of treating the fluorination catalyst obtained after the first step with a gaseous mixture comprising a reducing agent and an inert gas, said reducing agent being hydrogen or a $C_2$-$C_6$ hydrohalocarbon.

In a preferred embodiment, the steps (a) and (b) may be carried out alternately.

In a preferred embodiment, the steps (a) and (b) are carried out in a single reactor. Furthermore, the activation step as defined herein may also be carried out in the same reactor as that used for steps (a) and (b) according to the present process.

In a preferred embodiment, a purge of the reactor may be carried out before and/or after step (b), i.e. between the fluorination reaction and the regeneration step and/or between the end of the regeneration step and the fluorination reaction using the so-regenerated fluorination catalyst. Said purge may be carried out by maintaining the reactor under vacuum or by introducing a stream of nitrogen in the reactor in order to replace the gaseous components contained in the reactor before or after step b). Alternatively, the purge may be carried out by introducing a stream of an oxidizing agent such as air or a mixture of oxygen and nitrogen in the reactor in order to replace the gaseous components contained in the reactor before or after step b). The purge may be carried out at a temperature ranging from room temperature to 400° C.; preferably at an absolute pressure ranging from atmospheric pressure to 5 bar; and preferably for a time ranging from 1 hour to 50 hours.

In a second aspect, the present invention provides a process for the fluorination of a 2,3,3,3-tetrafluoropropene into 1,1,1,2,2-pentafluoropropane comprising the following steps:
  (a) contacting, in a reactor, 2,3,3,3-tetrafluoropropene with hydrogen fluoride in gas phase in the presence of a fluorination catalyst to produce 1,1,1,2,2-pentafluoropropane, and
  (b) regenerating the fluorination catalyst used in step a), wherein the step (b) of regenerating the fluorination catalyst comprises (c) the treatment of said fluorination catalyst with an oxidizing agent-containing gas flow to form an oxidized fluorination catalyst, and (d) the treatment of the oxidized fluorination catalyst obtained in step (c) with a gaseous mixture comprising a reducing agent; the catalyst regenerated in step b) being reused in step a) and the reducing agent being selected from the group consisting of hydrogen, carbon monoxide, nitrogen monoxide, formaldehyde, $C_1$-$C_6$ alkanes and $C_1$-$C_{10}$ hydrohalocarbons.

The reducing agent, the oxidizing agent, the catalyst, the regeneration step and the activation step are defined above and/or below with respect to the first aspect of the present invention.

DETAILED DESCRIPTION OF THE PRESENT INVENTION

The term "$C_1$-$C_{10}$ hydrohalocarbon" as used herein refers to a $C_1$-$C_{10}$ alkane, a $C_2$-$C_{10}$ alkene, a $C_2$-$C_{10}$ alkyne bearing at least one halogen atom, preferably the halogen atom is F or Cl. Preferably, $C_1$-$C_{10}$ hydrohalocarbon refers to a $C_2$-$C_6$ alkane or a $C_2$-$C_6$ alkene bearing at least one halogen atom, preferably F or Cl. More preferably, the $C_1$-$C_{10}$ hydrohalocarbon may be a chlorinated compound as defined hereunder, i.e. a $C_2$-$C_6$ alkane or a $C_2$-$C_6$ alkene bearing at least one chlorine atom. In particular, the $C_1$-$C_{10}$ hyrohalocarbon is a $C_3$ hydrohalocarbon comprising at least one chlorine atom.

The present invention relates to a process for the fluorination of a compound. It has been surprisingly found that by carrying out a regeneration of the fluorination catalyst used in the fluorination process the presence of by-products can be limited or avoided.

In a first aspect, the present invention therefore relates to a process for the fluorination of a chlorinated compound into a fluorinated compound. Said process comprises the steps of (a) contacting the chlorinated compound with hydrogen fluoride in gas phase in the presence of a fluorination catalyst to produce the fluorinated compound, and (b) regenerating said fluorination catalyst used in step (a). In particular, the step (b) of regenerating the fluorination catalyst comprises (c) the treatment of said fluorination catalyst with an oxidizing agent-containing gas flow to form an oxidized fluorination catalyst, and (d) the treatment of the oxidized fluorination catalyst obtained in step (c) with a gaseous mixture comprising a reducing agent.

The "chlorinated compound" can be any molecule having a chlorine atom, and the "fluorinated compound" can be any molecule having a fluorine atom.

Preferably, the chlorinated compound is a linear or branched $C_2$-$C_6$ alkane or $C_2$-$C_6$ alkene bearing at least one chlorine atom. The term "$C_2$-$C_6$ alkane" refers to an alkane having 2, 3, 4, 5 or 6 carbon atoms. The term "$C_2$-$C_6$ alkene" refers to an alkene having 2, 3, 4, 5 or 6 carbon atoms. The chlorinated compound may be a $C_2$-$C_5$ alkane, preferably a $C_2$-$C_4$ alkane, more preferably a $C_3$-$C_4$ alkane, most preferably a $C_3$ alkane, bearing at least one chlorine atom. The chlorinated compound may be a $C_2$-$C_5$ alkene, preferably a $C_2$-$C_4$ alkene, more preferably a $C_3$-$C_4$ alkene, most preferably a $C_3$ alkene, bearing at least one chlorine atom. Said chlorinated compound may bear at least one chlorine atom, preferably at least two chlorine atoms. Said chlorinated compound may bear one, two, three, four, five or six chlorine atoms. Hence, said chlorinated compound may be a linear or branched $C_2$-$C_6$ alkane or $C_2$-$C_6$ alkene bearing from one to six chlorine atoms, preferably from one to five chlorine atoms or from two to five chlorine atoms. The linear or branched $C_2$-$C_6$ alkane or $C_2$-$C_6$ alkene bearing at least one chlorine atom as defined herein may also bear one or more halogen atoms in addition to the chlorine atom(s), said halogen atom being selected from F, I and Br; preferably F. In a preferred embodiment, the total number of halogen atoms in the chlorinated compound as defined herein may be from 2 to 5 halogen atoms, preferably from 3 to 5 halogen atoms, more preferably from 4 to 5 halogen atoms selected from F, Cl, Br and I; at least one being a chlorine atom.

Preferably, the chlorinated compound may be a $C_3$ alkane compound having at least one chlorine atom, preferably at least two chlorine atoms; and preferably from 0 to 5 fluorine atoms. The chlorinated compound may be a $C_3$ alkane compound having one, two, three, four, five or six chlorine atoms; and preferably may have no fluorine atom, one, two, three, four or five fluorine atoms. Preferably, the chlorinated compound may be a $C_3$ alkane compound having four or five halogen atoms selected from Cl and F; at least one being a chlorine atom, preferably at least two being a chlorine atom. More preferably, the chlorinated compound may be a $C_3$ alkane compound having four or five halogen atoms selected from Cl and F, from which at most four halogen atoms are fluorine atoms, and at least one is a chlorine atom, preferably at least two are a chlorine atom.

Preferably, the chlorinated compound may be a $C_3$ alkene compound having at least one chlorine atom, preferably at least two chlorine atoms; and preferably from 0 to 3 fluorine atoms. The chlorinated compound may be a $C_3$ alkene compound having one, two, three or four chlorine atoms; and preferably may have no fluorine atom, one, two or three fluorine atoms. Preferably, the chlorinated compound may be a $C_3$ alkene compound having three or four halogen atoms selected from Cl and F; at least one being a chlorine atom, preferably at least two being a chlorine atom. More preferably, the chlorinated compound may be a $C_3$ alkene compound having three or four halogen atoms selected from Cl and F, from which at most three halogen atoms are fluorine atoms and at least one is a chlorine atom.

More preferably, the chlorinated compound may be selected from the group consisting of 2-chloro-3,3,3-trifluoro-1-propene (HFCO-1233 xf), 1,1,1,2,3-pentachloropropane (HCC-240db), 1,1,2,2,3-pentachloropropane (HCC-240aa), 2,3-dichloro-1,1,1-trifluoropropane (HCFC-243db), 1,1,2,3-tetrachloro-1-propene (HCO-1230xa), 2,3,3,3-tetrachloro-1-propene (HCO-1230xf), 2-chloro-1,1,1,2-tetrafluoropropane (HCFC-244bb), 1,1,1,3,3-pentachloropropane (HCC-240fa), 1,1,3,3-tetrachloropropene (HCO-1230za), 1,3,3,3-tetrachloropropene (HCO-1230zd), 1-chloro-3,3,3-trifluoropropene (HCFO-1233zd), 1,1,1,3-tetrachloropropane (HCC-250fb), 1,1,3-trichloropropene (HCO-1240za), 3,3,3-trichloropropene (HCO-1240zf).

In particular, the chlorinated compound may be selected from the group consisting of 2-chloro-3,3,3-trifluoro-1-propene (HFCO-1233xf), 1,1,1,2,3-pentachloropropane (HCC-240db), 1,1,2,2,3-pentachloropropane (HCC-240aa), 2,3-dichloro-1,1,1-trifluoropropane (HCFC-243db), 1,1,2,3-tetrachloro-1-propene (HCO-1230xa), 2,3,3,3-tetrachloro-1-propene (HCO-1230xf), 2-chloro-1,1,1,2-tetrafluoropropane (HCFC-244bb).

Preferably, the fluorinated compound is a linear or branched $C_2$-$C_6$ alkane or $C_2$-$C_6$ alkene bearing at least one fluorine atom. The fluorinated compound may be a $C_2$-$C_5$ alkane, preferably a $C_2$-$C_4$ alkane, more preferably a $C_3$-$C_4$ alkane, most preferably a $C_3$ alkane bearing at least one fluorine atom. The fluorinated compound may be a $C_2$-$C_5$ alkene, preferably a $C_2$-$C_4$ alkene, more preferably a $C_3$-$C_4$ alkene, most preferably a $C_3$ alkene bearing at least one fluorine atom.

Said fluorinated compound may be a linear or branched $C_2$-$C_6$ alkane or $C_2$-$C_6$ alkene bearing at least one fluorine atom, preferably at least two fluorine atoms, more preferably at least three fluorine atoms. The fluorinated compound may bear one, two, three, four or five fluorine atoms. The fluorinated compound may bear from one to five fluorine atoms, preferably from two to five fluorine atoms or from three to five fluorine atoms. The linear or branched $C_2$-$C_6$ alkane or $C_2$-$C_6$ alkene bearing at least one fluorine atom as defined herein may also bear one or more halogen atoms in addition to the fluorine atom(s), said halogen atom being selected from Cl, I and Br; preferably Cl. In a preferred embodiment, the total number of halogen atoms in the fluorinated compound as defined herein may be from 2 to 5 halogen atoms, preferably from 3 to 5 halogen atoms, more preferably from 4 or 5 halogen atoms selected from F, Cl, Br and I; at least one being a fluorine atom, preferably at least two being a fluorine atom, more preferably at least three being a fluorine atom.

Preferably, the fluorinated compound may be a $C_3$ alkane compound having at least one fluorine atom, preferably at least two fluorine atoms, more preferably at least three fluorine atoms. The fluorinated compound may be a $C_3$ alkane having one, two, three, four or five fluorine atoms; and preferably from 0 to 5 chlorine atoms, more preferably from 0 to 4 chlorine atoms, in particular from 0 to 3 chlorine atoms. Preferably, the fluorinated compound may be a $C_3$ alkane compound having four or five halogen atoms selected from Cl and F; at least one being a fluorine atom. More preferably, the fluorinated compound may be a $C_3$ alkane compound having four or five halogen atoms selected from Cl and F, from which at most three, preferably at most two, halogen atoms are chlorine atoms; and at least one is a fluorine atom, preferably at least two are a fluorine atom, more preferably at least three are a fluorine atom.

Preferably, the fluorinated compound may be a $C_3$ alkene compound having at least one fluorine atom, preferably at least two fluorine atoms, more preferably at least three fluorine atoms. The fluorinated compound may be a $C_3$ alkene compound having one, two, three or four fluorine atoms; and preferably from 0 to 2 chlorine atoms, more preferably from 0 to 1 chlorine atoms. Preferably, the fluorinated compound may be a $C_3$ alkene compound having four halogen atoms selected from Cl and F; at least one being a fluorine atom. More preferably, the fluorinated compound may be a $C_3$ alkene compound having four halogen atoms selected from Cl and F, from which at most two, preferably at most one, halogen atoms are chlorine atoms; and at least one is a fluorine atom, preferably at least two are a fluorine atom, more preferably at least three are a fluorine atom. In particular, the fluorinated compound may be a $C_3$ alkene compound having four halogen atoms, the latter being fluorine atoms. The fluorinated compound may also be a $C_3$ alkene compound having four halogen atoms, three out of four being fluorine atoms, the remaining halogen atoms being chlorine atoms.

More preferably, the fluorinated compound may be selected from the group consisting of 2,3,3,3-tetrafluoro-1-propene (HFO-1234yf), 2-chloro-1,1,1,2-tetrafluoropropane (HCFC-244bb), 1,1,1,2,2-pentafluoropropane (HFC-245cb), 1,1,1,3,3-pentafluoropropane (HFC-245fa), 1,1,1,3-tetrafluoro-3-chloropropane (HCFC-244fa), 1-chloro-3,3,3-trifluoropropene (HCFO-1233zd), 1,3,3,3-tetrafluoropropene (HFO-1234ze-E), 3,3,3-trifluoropropene (HFO-1243zf) and 2-chloro-3,3,3-trifluoro-1-propene (HFCO-1233xf).

According to the present process, the fluorination of the chlorinated compound lies in the increase of the degree of fluorination, i.e. the number of fluorine atoms in the fluorinated compound is greater than the number of fluorine atoms in the chlorinated compound. Preferably, during the reaction, at least one Cl substituent in the chlorinated compound is replaced by an F substituent. Preferably, the chlorinated compound selected for the reaction and the fluorinated compound obtained therefrom via the fluorination reaction have the same number of carbon atoms.

In a preferred embodiment, the fluorination of the chlorinated compound into a fluorinated compound is:
2-chloro-3,3,3-trifluoro-1-propene (HFCO-1233xf) to 2,3,3,3-tetrafluoro-1-propene (HFO-1234yf);

1,1,1,2,3-pentachloropropane (HCC-240db) to 2,3,3,3-tetrafluoro-1-propene (HFO-1234ye;
1,1,2,2,3-pentachloropropane (HCC-240aa) to 2,3,3,3-tetrafluoro-1-propene (HFO-1234ye;
2,3-dichloro-1,1,1-trifluoropropane (HCFC-243db) to 2,3,3,3-tetrafluoro-1-propene (HFO-1234yf);
1,1,2,3-tetrachloro-1-propene (HCO-1230xa) to 2,3,3,3-tetrafluoro-1-propene (HFO-1234ye;
2,3,3,3-tetrachloro-1-propene (HCO-1230xf) to 2,3,3,3-tetrafluoro-1-propene (HFO-1234ye;
1,1,1,2,3-pentachloropropane (HCC-240db) to 2-chloro-3,3,3-trifluoro-1-propene (HFCO-1233xf);
1,1,2,2,3-pentachloropropane (HCC-240aa) to 2-chloro-3,3,3-trifluoro-1-propene (HFCO-1233xf);
2,3-dichloro-1,1,1-trifluoropropane (HCFC-243db) to 2-chloro-3,3,3-trifluoro-1-propene (HFCO-1233xf);
1,1,2,3-tetrachloro-1-propene (HCO-1230xa) to 2-chloro-3,3,3-trifluoro-1-propene (HFCO-1233xf);
2,3,3,3-tetrachloro-1-propene (HCO-1230xf) to 2-chloro-3,3,3-trifluoro-1-propene (HFCO-1233xf);
2-chloro-3,3,3-trifluoro-1-propene (HFCO-1233xf) to 2-chloro-1,1,1,2-tetrafluoropropane (HCFC-244bb);
1,1,1,2,3-pentachloropropane (HCC-240db) to 2-chloro-1,1,1,2-tetrafluoropropane (HCFC-244bb);
1,1,2,2,3-pentachloropropane (HCC-240aa) to 2-chloro-1,1,1,2-tetrafluoropropane (HCFC-244bb);
2,3-dichloro-1,1,1-trifluoropropane (HCFC-243db) to 2-chloro-1,1,1,2-tetrafluoropropane (HCFC-244bb);
1,1,2,3-tetrachloro-1-propene (HCO-1230xa) to 2-chloro-1,1,1,2-tetrafluoropropane (HCFC-244bb);
2,3,3,3-tetrachloro-1-propene (HCO-1230xf) to 2-chloro-1,1,1,2-tetrafluoropropane (HCFC-244bb);
1,1,1,2,3-pentachloropropane (HCC-240db) to 1,1,1,2,2-pentafluoropropane (HFC-245cb);
1,1,2,2,3-pentachloropropane (HCC-240aa) to 1,1,1,2,2-pentafluoropropane (HFC-245cb);
2,3-dichloro-1,1,1-trifluoropropane (HCFC-243db) to 1,1,1,2,2-pentafluoropropane (HFC-245cb);
1,1,2,3-tetrachloro-1-propene (HCO-1230xa) to 1,1,1,2,2-pentafluoropropane (HFC-245cb);
2,3,3,3-tetrachloro-1-propene (HCO-1230xf) to 1,1,1,2,2-pentafluoropropane (HFC-245cb).

The conversion of the chlorinated compound to the fluorinated compound comprises direct conversion (i.e. in a single reaction step or under essentially one set of reaction conditions) and indirect conversion (i.e. through two or more reaction steps or using more than one single set of reaction conditions).

The fluorination reaction can be carried out with:
an HF molar ratio typically from 3:1 to 150:1, preferably from 4:1 to 125:1, more preferably from 5:1 to 100:1;
a contact time from 3 to 100 s, preferably from 4 to 75 s, more preferably from 5 to 50 s; and
a pressure ranging from atmospheric pressure to 20 bar, preferably from 2 to 18 bar, more preferably from 3 to 15 bar.

Step a) may be carried out at a temperature of from 200 to 450° C., preferably from 250° C. to 400° C., more preferably from 280° C. to 380° C. Preferably, the temperature of step a) is the catalyst bed temperature.

In order to prevent a fast deactivation of the catalyst during the fluorination reaction, an oxidizing agent (such as oxygen or chlorine) can be added, for example at a rate of from 0.05 to 20 mol. %, preferably of from 0.1 to 15 mol. %, more preferably of from 0.5 to 10 mol. %, in particular of from 1 to 8 mol. %, with respect to the mixture of oxidizing agent plus chlorinated compound.

In a preferred embodiment, a purge of the reactor may be carried out before regenerating the fluorination catalyst according to step (b) of the present invention. The purge may be carried out by maintaining the reactor under vacuum or by introducing a stream of nitrogen in the reactor after step (a) of the present process has been completed.

In a preferred embodiment, steps a) and b) can be carried out alternately. When step a) alternates with step b), the duration of each step can be from 50 to 2000 hours, advantageously from 50 to 1500 hours, preferably from 200 to 1000 hours, and the duration of each regeneration stage can be from 10 to 200 hours, preferably from 15 to 60 hours.

Catalyst

It can be for example a catalyst based on a metal including a transition metal oxide or a derivative or halide or oxyhalide of such a metal. Catalysts that can be used are chromium oxyfluoride, chromium oxides, chromium halides, aluminum fluoride and oxyfluoride, a supported or unsupported catalyst. Reference can also be made to the disclosures of WO-A-2007/079431, at page 7, lines 1-5 and 28-32, EP-A-939071, at paragraph [0022], WO 2008/054781 at page 9 line 22 to page 10 line 34, WO 2008/040969 in claim 1, all incorporated herein by reference.

In a preferred embodiment, the fluorination catalyst may comprise a chromium oxyfluoride, chromium oxides, chromium halides and mixtures thereof. The fluorination catalyst used in the present invention can be supported or unsupported. In a preferred embodiment, the chromium oxyfluoride catalyst may have a fluorine content of more than 30 wt % based on the total weight of the chromium oxyfluoride catalyst, preferably of from 30 to 45 wt %. Alternatively, the chromium oxyfluoride catalyst may have a fluorine content of less than 30 wt % based on the total weight of the chromium oxyfluoride catalyst.

The fluorination catalyst may be supported or unsupported chromium oxyfluoride, chromium oxides, chromium halides and mixtures thereof.

In a preferred embodiment, the catalyst is a supported mixed catalyst containing both chromium and nickel. The molar ratio Cr:Ni, with respect to the metallic element, is generally between 0.5 and 5, for example between 0.7 and 2, including close to 1. The catalyst may contain from 0.5 to 20 wt % of nickel.

As far as supported catalysts are concerned, the catalyst support can be selected from materials known in the art to be compatible with HF at higher temperature and pressure. For example, fluorinated alumina, prefluorinated activated carbon, graphite or fluorinated graphite are suitable catalyst supports. The support is preferably made from aluminum. There are several possible supports such as alumina, activated alumina or aluminum derivatives. These derivatives include aluminum halides and halide oxides of aluminum, for example described in U.S. Pat. No. 4,902,838, or obtained by the activation process. Reference can be made to WO 2009/118628, and especially to the disclosure of the catalyst from page 4, line 30 to page 7, line 16, which is incorporated herein by reference.

According to another embodiment, the process uses a high surface area Cr-based catalyst which is preferably unsupported. A preferred catalyst is a high surface area unsupported chromium oxide catalyst.

Any of the catalysts defined herein may have a surface area of at least 50 $m^2/g$, preferably of from 50 to 300 $m^2/g$, more preferably of from 70 to 250 $m^2/g$, in particular of from 100 to 200 $m^2/g$.

Other possible catalysts are the chromium dioxide-based fluorination catalysts comprising zinc or zinc oxide. The total amount of the zinc or of a compound of zinc present in the zinc/chromium dioxide catalysts may be from about 0.01% to about 25%, preferably 0.1% to 25%, conveniently 0.01% to 6% zinc, and in some embodiments preferably 0.5% by weight to 25% by weight of the catalyst, preferably from about 1 to 10% by weight of the catalyst, more preferably from about 2 to 8% by weight of the catalyst, for example about 4 to 6% by weight of the catalyst. In other embodiments, the catalyst conveniently comprises 0.01% to 1%, more preferably 0.05% to 0.5% zinc. The zinc/chromium dioxide catalysts may include an additional metal or compound thereof. Typically, the additional metal is a divalent or trivalent metal, preferably selected from nickel, magnesium, aluminium and mixtures thereof. Typically, the additional metal is present in an amount of from 0.01% by weight to about 25% by weight of the catalyst, preferably from about 0.01 to 10% by weight of the catalyst. Other embodiments may comprise at least about 0.5% by weight or at least about 1% by weight of additional metal. Other catalysts are chromium dioxide-based fluorination catalysts consisting of amorphous chromium dioxide; zinc oxide in a total amount of zinc of from 0.5 to 25% by weight of the catalyst; and crystalline chromium oxide in a total amount of from 0.1 to 2.5% by weight of the catalyst; the catalyst being supported or unsupported, as disclosed in EP 1 877 181.

In a preferred embodiment, the catalyst can contain, preferably at a low level, one or more co-catalysts such as a Co, Zn, Mn, Mg, V, Mo, Te, Nb, Sb, Ta, P and Ni salt. A preferred co-catalyst may be nickel, magnesium or zinc. The preferred unsupported chromium catalyst can optionally contain low levels of one or more co-catalysts selected from cobalt, nickel, zinc, manganese, magnesium or a mixture of manganese and magnesium, prepared by processes known in the art, such as impregnation, mixed powder and the like.

The amount of co-catalyst, when present, can be varied from 1 to 20 wt. %, preferably from 1 to 10 wt. %, more preferably from 1 to 5 wt. %. The co-catalyst can be added to the catalyst by processes known in the art such as adsorption from an aqueous or organic solution, followed by solvent evaporation. The preferred catalyst in this embodiment is pure chromium oxide with nickel or zinc as a co-catalyst. Alternatively, the co-catalyst can be physically mixed with the catalyst via grinding to produce an intimate mixture.

Before activation, the catalyst may be subjected to a drying step. Said drying step may include passing a drying gas, preferably nitrogen, over the catalyst. The drying step can be carried out at a pressure of from atmospheric pressure up to 20 bar. The temperature of the catalyst during the drying step can range from room temperature up to 400° C., preferably from about 100° C. to about 300° C. at a contact time from about 1 to 100 s, preferably from about 10 to 40 s, for approximately 1 to 50 hours, preferably between 5 to 20 hours. After the drying step, the catalyst can be activated in order to reach a better level of catalyst activity.

Activation of the Catalyst

The present inventors have found that the activation of the above catalysts using an oxidizing agent-containing gas flow may improve the efficiency of the fluorination process.

The activation process comprises activating the catalyst using one activating agent or two activating agents, in two steps or in a single step. One of the activating agents is an oxidizing agent, such as oxygen or an oxygen/nitrogen mixture or air or chlorine. The other activating agent can be a gaseous mixture comprising a reducing agent.

In a first embodiment, the activation process comprises a step of contacting the fluorination catalyst with an oxidizing agent-containing gas flow. The fluorination catalyst is treated with the oxidizing agent. The oxidizing agent may be an oxygen-containing agent, preferably selected from air, oxygen, chlorine or a mixture of oxygen and nitrogen. The temperature during the treatment with the oxidizing agent may range from 250 to 500° C., preferably from 300 to 450° C., more preferably from 350 to 400° C.; preferably with a contact time of from about 1 to about 200 s, preferably from 1 to 150 s, more preferably from 5 to 100 s; and preferably for a time of at least 1 hour, preferably at least 2 hours, more preferably at least 4 hours, most preferably at least 10 hours, in particular at least 15 hours. Hence, the treatment with the oxidizing agent may be carried out for a time of from 1 to about 1500 hours, preferably from 2 to 1000 hours, more preferably from 4 to 500 hours, most preferably from 10 to 200 hours, in particular from 15 to 150 hours.

In another embodiment, the activation step comprises a first step (i) of contacting the fluorination catalyst with an oxidizing agent-containing gas flow, as defined above, and a second step (ii) of treating the fluorination catalyst obtained after step (i) with a gaseous mixture comprising a reducing agent.

The gaseous mixture comprising the reducing agent may also comprise an inert gas. The inert gas may be nitrogen, helium, argon, HF or mixtures thereof. Alternatively, the inert gas may comprise nitrogen, helium, argon or mixtures thereof. The gaseous mixture may comprise from 1 to 10% by volume of reducing agent, preferably of from 2 to 9% by volume, more preferably from 3 to 7% by volume based on the total volume of the gaseous mixture.

The reducing agent may be selected from the group consisting of hydrogen, carbon monoxide, nitrogen monoxide, formaldehyde, $C_1$-$C_6$ alkanes and $C_1$-$C_{10}$ hydrohalocarbons. Preferably, the reducing agent may be hydrogen, formaldehyde, a $C_1$-$C_6$ alkane or a $C_1$-$C_{10}$ hydrohalocarbon. In particular, the reducing agent may be a $C_1$-$C_{10}$ hydrohalocarbon, preferably a chlorinated compound as defined above. When the reducing agent is a chlorinated compound, it may be the same or different from the chlorinated compound used in step a) of the present process, preferably the same as the one used in step a) of the present process. When the reducing agent is a $C_1$-$C_{10}$ hydrohalocarbon, preferably a chlorinated compound, the gaseous mixture comprises an inert gas such as nitrogen, helium, argon, HF or mixtures thereof. Preferably, when the reducing agent is a $C_1$-$C_{10}$ hydrohalocarbon, in particular a $C_3$ hydrohalocarbon, the gaseous mixture comprises HF.

Hence, the reducing agent may be a $C_3$ alkane compound having at least one chlorine atom, preferably at least two chlorine atoms; and preferably from 0 to 5 fluorine atoms. The reducing agent may be a $C_3$ alkane compound having one, two, three, four, five or six chlorine atoms; and preferably may have no fluorine atom, one, two, three, four or five fluorine atoms. Preferably, the reducing agent may be a $C_3$ alkane compound having four or five halogen atoms selected from Cl and F; at least one being a chlorine atom, preferably at least two being a chlorine atom. More preferably, the reducing agent may be a $C_3$ alkane compound having four or five halogen atoms selected from Cl and F; from which at most four halogen atoms are fluorine atoms, and at least one is a chlorine atom, preferably at least two are a chlorine atom.

Preferably, the reducing agent may be a $C_3$ alkene compound having at least one chlorine atom, preferably at least two chlorine atoms; and preferably from 0 to 3 fluorine atoms. The reducing agent may be a $C_3$ alkene compound having one, two, three or four chlorine atoms; and preferably may have no fluorine atom, one, two or three fluorine atoms. Preferably, the reducing agent may be a $C_3$ alkene compound having four halogen atoms selected from Cl and F; at least one being a chlorine atom, preferably at least two being a chlorine atom. More preferably, the reducing agent may be a $C_3$ alkene compound having four halogen atoms selected from Cl and F; from which at most three halogen atoms are fluorine atoms, and at least one is a chlorine atom.

More preferably, the reducing agent may be selected from the group consisting of 2-chloro-3,3,3-trifluoro-1-propene (HFCO-1233xf), 1,1,1,2,3-pentachloropropane (HCC-240db), 1,1,2,2,3-pentachloropropane (HCC-240aa), 2,3-dichloro-1,1,1-trifluoropropane (HCFC-243db), 1,1,2,3-tetrachloro-1-propene (HCO-1230xa), 2,3,3,3-tetrachloro-1-propene (HCO-1230xf), 2-chloro-1,1,1,2-tetrafluoropropane (HCFC-244bb), 1,1,1,3,3-pentachloropropane (HCC-240fa), 1,1,3,3-tetrachloropropene (HCO-1230za), 1,3,3,3-tetrachloropropene (HCO-1230zd), 1-chloro-3,3,3-trifluoropropene (HCFO-1233 zd), 1,1,1,3-tetrachloropropane (HCC-250fb), 1,1,3-trichloropropene (HCO-1240za), 3,3,3-trichloropropene (HCO-1240zf).

In particular, the reducing agent may be selected from the group consisting of 2-chloro-3,3,3-trifluoro-1-propene (HFCO-1233xf), 1,1,1,2,3-pentachloropropane (HCC-240db), 1,1,2,2,3-pentachloropropane (HCC-240aa), 2,3-dichloro-1,1,1-trifluoropropane (HCFC-243db), 1,1,2,3-tetrachloro-1-propene (HCO-1230xa), 2,3,3,3-tetrachloro-1-propene (HCO-1230xf), 2-chloro-1,1,1,2-tetrafluoropropane (HCFC-244bb).

The temperature of the second step (ii) may be from about 100° C. to about 450° C. The second step (ii) may be carried out with a contact time of from about 1 to about 100 s, preferably of from 1 to 75 s, more preferably of from 5 to 50 s; for a time greater than 1 hour, preferably from 1 to 50 hours. Preferably, the temperature of the second step (ii) may be from about 300 to about 400° C., with a contact time of from about 1 to about 100 s, preferably of from 1 to 75 s, more preferably of from 5 to 50 s; for a time greater than 1 hour, preferably from 1 to 50 hours. Alternatively, the second step (ii) may be carried out for a time lower than 1 hour. Alternatively, the second step (ii) may be carried out at a temperature ranging from 200 to 300° C. The second step (ii) may be carried out at a pressure ranging from atmospheric pressure to 5 bar.

Both steps (i) and (ii) can be repeated, until the catalyst activity reaches its best level.

In a particular embodiment, before the activation process as defined above, the catalyst may be contacted with a mixture comprising HF and a chlorinated compound as defined herein. The contacting can be carried out for about 6 to about 100 hours (for example for less than 50 hours). The HF:chlorinated compound molar ratio can range from about 2 to about 40. The chlorinated compound may be the same as the one subsequently used during the fluorination reaction in step a). Alternatively, the chlorinated compound may be different from the chlorinated compound which is subsequently used during the fluorination reaction. Hence, in this particular embodiment, the activation step may be carried out by:
  (i') contacting the fluorination catalyst with a mixture comprising HF and a chlorinated compound,
  (ii') contacting the fluorination catalyst obtained in step (i') with an oxidizing agent-containing gas flow, and
  (iii') optionally or not, treating the fluorination catalyst obtained after step (ii') with the reducing agent.

Each step can be repeated, until the catalyst activity reaches its best level.

According to another embodiment, the activation process may be carried out by:
  (i") contacting the fluorination catalyst with a gaseous mixture comprising HF, an oxidizing agent-containing gas flow and a chlorinated compound, and
  (ii') optionally or not, contacting the fluorination catalyst obtained in step (i") with a reducing agent.

The oxidizing agent, the chlorinated compound and the reducing agent are as defined above. The proportion of oxidizing agent in the mixture of HF, chlorinated compound and oxidizing agent can range from about 2 to about 98 mol. %. The proportion of chlorinated compound in the mixture of HF, chlorinated compound and oxidizing agent can range from about 2 to about 98 mol. %. The proportion of HF in the mixture of HF, chlorinated compound and oxidizing agent can range from about 2 to about 98 mol. %. The process conditions of the activation step are defined above. Each step can be repeated, until the catalyst activity reaches its best level.

The steps (i), (ii), or (i'), (ii'), (iii'), or (i"), (ii") can be repeated one, two or more times in an alternated manner.

Regeneration of the Catalyst

The present inventors have also found that the presence of by-products can be limited by subjecting the catalyst to regeneration steps wherein it is contacted with an oxidizing agent-containing gas flow and subsequently with a reducing agent.

In a preferred embodiment, the regeneration of the fluorination catalyst (step b) of the present process comprises:
  c) the treatment of said fluorination catalyst with an oxidizing agent-containing gas flow to form an oxidized fluorination catalyst; and
  d) the treatment of said oxidized fluorination catalyst obtained in step c) with a gaseous mixture comprising a reducing agent.

According to one embodiment, the oxidizing agent used in step c) is oxygen or air or an oxygen/nitrogen mixture or chlorine. When step c) is carried out with air or an oxygen/nitrogen mixture, the proportion of oxygen can range from 20 to about 100 mol. % relative to the mixture of oxygen plus nitrogen.

In another embodiment, step c) can be carried out with oxygen or air or an oxygen/nitrogen mixture or chlorine and HF. The proportion of oxygen can range from about 2 to about 98 mol. % relative to the mixture of oxygen plus HF, and from about 20 to about 100 mol. % relative to the mixture of oxygen plus nitrogen.

The temperature during step c) may range from 250 to 500° C., preferably from 300 to 450° C., more preferably from 350 to 400° C. or from 325° C. to 375° C.; with a contact time of from 1 to 200 s, preferably from 1 to 150 s, more preferably from 5 to 100 s; and for a time of from 1 to about 1500 hours, preferably from 2 to 1000 hours, more preferably from 4 to 500 hours, most preferably from 10 to 200 hours, in particular from 15 to 150 hours, more particularly from 15 to 70 hours. The step c) can be carried out at a pressure ranging from atmospheric pressure to 20 bar, advantageously from atmospheric pressure to 5 bar, preferably from atmospheric pressure to 3 bar. In a preferred embodiment, the temperature during step c) can range from about 250 to 500° C., with a contact time of from about 1 to 200 s, for a time of from 10 to 200 hours and at a pressure ranging from atmospheric pressure to 20 bar, preferably from atmospheric pressure to 3 bar. According to one particularly preferred embodiment, the temperature during step c) may be from about 325 to 375° C., with a contact time of from about 5 to 100 s, for a time of from 15 to 75 hours and at a pressure ranging from atmospheric pressure to 20 bar, preferably from atmospheric pressure up to 3 bar.

The gaseous mixture used in step (d) may comprise an inert gas, in particular when the reducing agent is a $C_1$-$C_{10}$ hydrohalocarbon, preferably a chlorinated compound. The inert gas may be nitrogen, helium, argon, HF or mixtures thereof. The inert gas may be nitrogen, helium, argon, or mixtures thereof. In particular, the inert gas may be a mixture of HF and nitrogen. More particularly, the inert gas may be a mixture of HF and nitrogen when the reducing agent is a $C_1$-$C_{10}$ hydrohalocarbon, advantageously a $C_3$ hydrohalocarbon, preferably a $C_3$ alkane or alkene having at least one chlorine atom.

In a preferred embodiment, the gaseous mixture of step (d) comprises from 1 to 10% by volume of reducing agent, preferably from 2 to 9% by volume, more preferably from 3 to 7% by volume based on the total volume of the gaseous mixture.

In a preferred embodiment, step d) is carried out with a reducing agent selected from the group consisting of hydrogen, carbon monoxide, nitrogen monoxide, formaldehyde, $C_1$-$C_6$ alkanes and $C_1$-$C_{10}$ hydrohalocarbons. Preferably, the reducing agent may be hydrogen, formaldehyde, a $C_1$-$C_6$ alkane or a $C_1$-$C_{10}$ hydrohalocarbon. More preferably, the reducing agent may be a $C_1$-$C_{10}$ hydrohalocarbon. In particular, the reducing agent may be a chlorinated compound as defined above. More particularly, the reducing agent may be hydrogen or a $C_3$ alkane or alkene having at least one chlorine atom.

Hence, the reducing agent may be a $C_3$ alkane compound having at least one chlorine atom, preferably at least two chlorine atoms; and preferably from 0 to 5 fluorine atoms. The reducing agent may be a $C_3$ alkane compound having one, two, three, four, five or six chlorine atoms; and preferably may have no fluorine atom, one, two, three, four or five fluorine atoms. Preferably, the reducing agent may be a $C_3$ alkane compound having four or five halogen atoms selected from Cl and F; at least one being a chlorine atom, preferably at least two being a chlorine atom. More preferably, the reducing agent may be a $C_3$ alkane compound having four or five halogen atoms selected from Cl and F, from which at most four halogen atoms are fluorine atoms, and at least one is a chlorine atom, preferably at least two are a chlorine atom.

Preferably, the reducing agent may be a $C_3$ alkene compound having at least one chlorine atom, preferably at least two chlorine atoms; and preferably from 0 to 3 fluorine atoms. The reducing agent may be a $C_3$ alkene compound having one, two, three or four chlorine atoms; and preferably may have no fluorine atom, one, two or three fluorine atoms. Preferably, the reducing agent may be a $C_3$ alkene compound having four halogen atoms selected from Cl and F; at least one being a chlorine atom, preferably at least two being a chlorine atom. More preferably, the reducing agent may be a $C_3$ alkene compound having four halogen atoms selected from Cl and F, from which at most three halogen atoms are fluorine atoms, and at least one is a chlorine atom.

More preferably, the reducing agent may be selected from the group consisting of 2-chloro-3,3,3-trifluoro-1-propene (HFCO-1233xf), 1,1,1,2,3-pentachloropropane (HCC-240db), 1,1,2,2,3-pentachloropropane (HCC-240aa), 2,3-dichloro-1,1,1-trifluoropropane (HCFC-243db), 1,1,2,3-tetrachloro-1-propene (HCO-1230xa), 2,3,3,3-tetrachloro-1-propene (HCO-1230xf), 2-chloro-1,1,1,2-tetrafluoropropane (HCFC-244bb), 1,1,1,3,3-pentachloropropane (HCC-240fa), 1,1,3,3-tetrachloropropene (HCO-1230za), 1,3,3,3-tetrachloropropene (HCO-1230zd), 1-chloro-3,3,3-trifluoropropene (HCFO-1233 zd), 1,1,1,3-tetrachloropropane (HCC-250fb), 1,1,3-trichloropropene (HCO-1240za), 3,3,3-trichloropropene (HCO-1240zf).

In particular, the reducing agent may be selected from the group consisting of 2-chloro-3,3,3-trifluoro-1-propene (HFCO-1233xf), 1,1,1,2,3-pentachloropropane (HCC-240db), 1,1,2,2,3-pentachloropropane (HCC-240aa), 2,3-dichloro-1,1,1-trifluoropropane (HCFC-243db), 1,1,2,3-tetrachloro-1-propene (HCO-1230xa), 2,3,3,3-tetrachloro-1-propene (HCO-1230xf), 2-chloro-1,1,1,2-tetrafluoropropane (HCFC-244bb).

Step d) may be carried out at a temperature ranging from about 100° C. to about 450° C. Preferably, step d) may be carried out at a temperature of from 300 to 400° C., in particular of from 325° C. to 375° C. Step d) may be carried out for a contact time of from about 1 to about 100 s, preferably of from 1 to 75 s, more preferably of from 5 to 50 s. Preferably, step d) may be carried out for a time greater than 1 hour, preferably from 1 to 50 hours, in particular from 1 to 15 hours. More preferably, step d) may be carried out at a temperature of from 300 to 400° C., in particular of from 325° C. to 375° C., with a contact time of from about 1 to about 100 s, preferably of from 1 to 75 s, more preferably of from 5 to 50 s; for a time greater than 1 hour, preferably from 1 to 50 hours, in particular from 1 to 15 hours. Alternatively, step d) may be carried out for a time lower than 1 hour. Alternatively, step d) may be carried out at a temperature ranging from 200 to 300° C. The step d) may be carried out at a pressure ranging from atmospheric pressure to 5 bar.

Both steps c) and d) can be repeated one, two or more times in an alternated manner. In particular, step d) may be independently repeated one, two or more times, i.e. each step d) may be repeated with different reducing agents. For example, step d) may be carried out with hydrogen and may be repeated with 2-chloro-3,3,3-trifluoro-1-propene.

EXAMPLES

The following examples illustrate the invention without limiting it.

The equipment comprised a tubular reactor made of INCONEL® 600 alloy having an internal diameter of 21 mm and a 12 m coil pre-heater having an internal diameter of 6 mm. The system was dipped in a fluidized sand bath. The reactor was equipped with pressure and temperature controllers. The reactants, preliminarily mixed, were introduced at the bottom of the reactor.

The gaseous stream exiting the reactor was passed through a water scrubber before being dried, sampled and analyzed by gas chromatography. A HP model 5890 GC was used for all experiments. The chromatograph was equipped with an RTX®-200 column and a ShinCarbon column (Restek) both connected to a thermal conductivity detector (TCD).

Comparative Example 1

Fluorination of HFCO-1233xf—Regeneration of the fluorination catalyst without treatment with a gaseous mixture comprising a reducing agent.

The above-described equipment was used to perform the catalytic vapor phase fluorination of HFCO-1233xf. The reactor was charged with about 130 cm³ of a previously activated commercial chromium bulk catalyst.

The reaction was run at a constant absolute pressure of P=5 bar and the temperature was maintained at T=380° C. Anhydrous hydrogen fluoride (HF), HFCO-1233xf and air were continuously introduced into the reactor. The molar ratio of HF to HFCO-1233xf was 20. The molar ratio of oxygen ($O_2$) to HFCO-1233xf was 0.04. The contact time was calculated as 20 sec under the reaction conditions.

After 70 hours of reaction, while the conversion of HFCO-1233xf was about 20%, the reaction was stopped and a regeneration step was performed with an air treatment for 72 hours at 13 l/h, T=380° C. and atmospheric pressure.

Then the reaction was restarted using the same conditions.

The major product obtained other than HFO-1234yf is HFC-245cb. This compound can be recycled and reused and is regarded as a useful substance. The by-products obtained and their selectivities are shown in table 1 below:

TABLE 1

| Time (h) | Selectivities | | | | |
|---|---|---|---|---|---|
| | CO | F143a | F1234yf + F245cb | F1234zeZ + F245fa | F1233zdE | Others |
| 6 | 2.26 | 0.56 | 86.17 | 2.78 | 2.16 | 2.24 |
| 12 | 2.13 | 0.54 | 87.22 | 2.53 | 1.89 | 2.09 |
| 24 | 2.00 | 0.46 | 89.61 | 1.83 | 1.47 | 1.58 |
| 30 | 2.30 | 0.45 | 89.05 | 1.74 | 1.34 | 1.72 |
| 36 | 2.06 | 0.45 | 89.90 | 1.60 | 1.15 | 1.67 |

Example 2 According to the Present Invention

Fluorination of HFCO-1233xf—Regeneration of the fluorination catalyst with treatment with a gaseous mixture comprising a reducing agent.

The above-described equipment was used to perform the catalytic vapor phase fluorination of HFCO-1233xf. The reactor was charged with about 130 cm$^3$ of a previously activated commercial chromium bulk catalyst.

The reaction was run at a constant absolute pressure of P=5 bar and the temperature was maintained at T=380° C. Anhydrous hydrogen fluoride (HF), HFCO-1233xf and air were continuously introduced into the reactor. The molar ratio of HF to HFCO-1233xf was 20. The molar ratio of oxygen ($O_2$) to HFCO-1233xf was 0.04. The contact time was calculated as 20 sec under the reaction conditions.

After 76 hours of reaction, while the conversion of HFCO-1233xf was about 35%, the reaction was stopped and a regeneration step was performed
  with an air treatment for 72 hours at 5 l/h, T=380° C. and atmospheric pressure,
  with a treatment using a mixture of HFCO-1233xf:HF: nitrogen (14.1 g/h, 43.1 g/h; 51 l/h) for 5 hours at T=350° C.

Then the reaction was restarted using the same conditions.

The major product obtained other than HFO-1234yf is HFC-245cb. This compound can be recycled and reused and is regarded as a useful substance. The by-products obtained and their selectivities are shown in table 2 below:

TABLE 2

| Time (h) | Selectivities | | | | |
|---|---|---|---|---|---|
| | CO | F143a | F1234yf + F245cb | F1234zeZ + F245fa | F1233zdE | Others |
| 6 | 2.05 | 0.45 | 89.32 | 1.69 | 1.53 | 0.26 |
| 12 | 1.99 | 0.45 | 89.70 | 1.60 | 1.40 | 0.27 |
| 24 | 1.90 | 0.40 | 90.66 | 1.39 | 1.21 | 0.31 |
| 30 | 2.01 | 0.42 | 90.23 | 1.46 | 1.15 | 0.35 |
| 36 | 2.02 | 0.42 | 90.28 | 1.41 | 1.11 | 0.36 |

Comparative Example 3

Fluorination of HFCO-1233xf—Regeneration of the fluorination catalyst without treatment with a gaseous mixture comprising a reducing agent.

The above-described equipment was used to perform the catalytic vapor phase fluorination of HFCO-1233xf. The reactor was charged with about 130 cm$^3$ of a previously activated commercial chromium bulk catalyst.

The reaction was run at a constant absolute pressure of P=5 bar and the temperature was maintained at T=350° C. Anhydrous hydrogen fluoride (HF), HFCO-1233xf and air were continuously introduced into the reactor. The molar ratio of HF to HFCO-1233xf was 20. The molar ratio of oxygen ($O_2$) to HFCO-1233xf was 0.04. The contact time was calculated as 34 sec under the reaction conditions.

After 48 hours of reaction, the flow rates of the reactants were increased and the new contact time was calculated as 20 sec under the reaction conditions. After another 24 hours of reaction, while the conversion of HFCO-1233xf was about 45%, the reaction was stopped and a regeneration step was performed with an air treatment for 72 hours at 7.5 l/h, T=350° C. and atmospheric pressure.

Then the reaction was restarted using the same conditions (contact time calculated as sec under the reaction conditions).

The major product obtained other than HFO-1234yf is HFC-245cb. This compound can be recycled and reused and is regarded as a useful substance. The by-products obtained and their selectivities are shown in table 3 below:

TABLE 3

| Time (h) | Selectivities | | | | |
|---|---|---|---|---|---|
| | F1234yf + F245cb | F1234zeE + F1243zf | F1234zeZ + F245fa | F1224xe | F1233zdE |
| 6 | 92.41 | 0.95 | 1.25 | 0.33 | 0.89 |
| 12 | 93.04 | 0.99 | 1.40 | 0.13 | 1.08 |
| 18 | 94.18 | 0.80 | 1.16 | 0.08 | 0.80 |

Example 4 According to the Present Invention

Fluorination of HFCO-1233xf—Regeneration of the fluorination catalyst with treatment with a gaseous mixture comprising a reducing agent.

The above-described equipment was used to perform the catalytic vapor phase fluorination of HFCO-1233xf. The reactor was charged with about 130 cm$^3$ of a previously activated commercial chromium bulk catalyst.

The reaction was run at a constant absolute pressure of P=5 bar and the temperature was maintained at T=350° C. Anhydrous hydrogen fluoride (HF), HFCO-1233xf and air were continuously introduced into the reactor. The molar ratio of HF to HFCO-1233xf was 20. The molar ratio of oxygen ($O_2$) to HFCO-1233xf was 0.04. The contact time was calculated as 20 sec under the reaction conditions.

After 48 hours of reaction, while the conversion of HFCO-1233xf was about 61%, the reaction was stopped and a regeneration step was performed
  with an air treatment for 48 hours at 5 l/h, T=350° C. and atmospheric pressure,
  with a treatment using a mixture of hydrogen:nitrogen (1.25 l/h; 25 l/h) for 5 hours at T=325° C.
  with a nitrogen treatment for 24 hours at 10 l/h, T=350° C. and absolute pressure P=1.6 bar.

Then the reaction was restarted using the same conditions.

The major product obtained other than HFO-1234yf is HFC-245cb. This compound can be recycled and reused and is regarded as a useful substance. The by-products obtained and their selectivities are shown in table 4 below:

TABLE 4

| | Selectivities | | | |
|---|---|---|---|---|
| Time (h) | F1234yf + F245cb | F1234zeE + F1243zf | F1234zeZ + F245fa | F1224xe | F1233zdE |
| 6 | 95.63 | 0.51 | 0.67 | 0.07 | 0.44 |
| 18 | 95.01 | 0.57 | 0.78 | 0.07 | 0.47 |

The invention claimed is:

1. Process for the fluorination of a chlorinated C3 alkane or alkene compound having at least one chlorine atom into a fluorinated C3 alkane or alkene compound having at least one fluorine atom comprising the following steps:
   a. contacting, in a reactor, the chlorinated compound with hydrogen fluoride in gas phase in the presence of a fluorination catalyst to produce a fluorinated compound, and
   b. regenerating the fluorination catalyst used in step a), wherein the step (b) of regenerating the fluorination catalyst comprises (c) the treatment of said fluorination catalyst with an oxidizing agent-containing gas flow to form an oxidized fluorination catalyst, and (d) the treatment of the oxidized fluorination catalyst obtained in step (c) with a gaseous mixture comprising a reducing agent and an inert gas; the catalyst regenerated in step b) being reused in step a) and the reducing agent being selected from the group consisting of $C_1$-$C_{10}$ hydrohalocarbons.

2. Process for the fluorination of a chlorinated C3 alkane or alkene compound having at least one chlorine atom into a fluorinated C3 alkane or alkene compound having at least one fluorine atom comprising the following steps:
   (a) contacting, in a reactor, the chlorinated compound with hydrogen fluoride in gas phase in the presence of a fluorination catalyst to produce a fluorinated compound, and
   (b) regenerating the fluorination catalyst used in step a), wherein the step (b) of regenerating the fluorination catalyst comprises (c) the treatment of said fluorination catalyst with an oxidizing agent-containing gas flow to form an oxidized fluorination catalyst, and (d) the treatment of the oxidized fluorination catalyst obtained in step (c) with a gaseous mixture comprising a reducing agent; the catalyst regenerated in step b) being reused in step a) and the reducing agent being selected from the group consisting of $C_1$-$C_{10}$ hydrohalocarbons.

3. Process according to claim 1, wherein the reducing agent is selected from the group consisting of $C_2$-$C_6$ hydrohalocarbons.

4. Process according to claim 1, wherein the inert gas is selected from nitrogen, helium, argon, or mixtures thereof.

5. Process according to claim 1, wherein the gaseous mixture comprises HF.

6. Process according to claim 1, wherein the gaseous mixture of step (d) comprises from 1 to 10% by volume of reducing agent based on the total volume of the gaseous mixture.

7. Process according to claim 1, wherein the gaseous mixture from step (d) comprises hydrogen and nitrogen or argon or the gaseous mixture from step (d) comprises a C2-C6 hydrohalocarbon, nitrogen or argon, and HF.

8. Process according to claim 1, wherein step d) is carried out at a temperature ranging from 100° C. to 450° C., with a contact time of from 1 to 100 s.

9. Process according to claim 1, wherein the chlorinated compound is 2-chloro-3,3,3-trifluoro-1-propene (HFCO-1233xf), 1,1,1,2,3-pentachloropropane (HCC-240db), 1,1,2,2,3-pentachloropropane (HCC-240aa), 2,3-dichloro-1,1,1-trifluoropropane (HCFC-243db), 1,1,2,3-tetrachloro-1-propene (HCO-1230xa), 2,3,3,3-tetrachloro-1-propene (HCO-1230xf), 2-chloro-1,1,1,2-tetrafluoropropane (HCFC-244bb), 1,1,1,3,3-pentachloropropane (HCC-240fa), 1,1,3,3-tetrachloropropene (HCO-1230za), 1,3,3,3-tetrachloropropene (HCO-1230zd), 1-chloro-3,3,3-trifluoropropene (HCFO-1233zd), 1,1,1,3-tetrachloropropane (HCC-250fb), 1,1,3-trichloropropene (HCO-1240za), 3,3,3-trichloropropene (HCO-1240zf); more preferably the chlorinated compound is selected from the group consisting of 2-chloro-3,3,3-trifluoro-1-propene (HFCO-1233xf), 1,1,1,2,3-pentachloropropane (HCC-240db), 1,1,2,2,3-pentachloropropane (HCC-240aa), 2,3-dichloro-1,1,1-trifluoropropane (HCFC-243db), 1,1,2,3-tetrachloro-1-propene (HCO-1230xa), 2,3,3,3-tetrachloro-1-propene (HCO-1230xf) or 2-chloro-1,1,1,2-tetrafluorocarbons (HCFC-244bb).

10. Process according to claim 1, wherein the fluorinated compound is 2,3,3,3-tetrafluoro-1-propene (HFO-1234yf), 2-chloro-1,1,1,2-tetrafluoropropane (HCFC-244bb), 1,1,1,2,2-pentafluoropropane (HFC-245cb), 1,1,1,3,3-pentafluoropropane (HFC-245fa), 1,1,1,3-tetrafluoro-3-chloropropane (HCFC-244fa), 1-chloro-3,3,3-trifluoropropene (HCFO-1233zd), 1,3,3,3-tetrafluoropropene (HFO-1234ze), 3,3,3-trifluoropropene (HFO-1243zf) or 2-chloro-3,3,3-trifluoro-1-propene (HFCO-1233xf).

11. Process according to claim 1, wherein the fluorination of the chlorinated compound into a fluorinated compound is:
   2-chloro-3,3,3-trifluoro-1-propene (HFCO-1233xf) to 2,3,3,3-tetrafluoro-1-propene (HFO-1234yf);
   1,1,1,2,3-pentachloropropane (HCC-240db) to 2,3,3,3-tetrafluoro-1-propene (HFO-1234yf);
   1,1,2,2,3-pentachloropropane (HCC-240aa) to 2,3,3,3-tetrafluoro-1-propene (HFO-1234yf);
   2,3-dichloro-1,1,1-trifluoropropane (HCFC-243db) to 2,3,3,3-tetrafluoro-1-propene (HFO-1234yf);
   1,1,2,3-tetrachloro-1-propene (HCO-1230xa) to 2,3,3,3-tetrafluoro-1-propene (HFO-1234yf);
   2,3,3,3-tetrachloro-1-propene (HCO-1230xf) to 2,3,3,3-tetrafluoro-1-propene (HFO-1234yf);
   1,1,1,2,3-pentachloropropane (HCC-240db) to 2-chloro-3,3,3-trifluoro-1-propene (HFCO-1233xf);
   1,1,2,2,3-pentachloropropane (HCC-240aa) to 2-chloro-3,3,3-trifluoro-1-propene (HFCO-1233xf);
   2,3-dichloro-1,1,1-trifluoropropane (HCFC-243db) to 2-chloro-3,3,3-trifluoro-1-propene (HFCO-1233xf);
   1,1,2,3-tetrachloro-1-propene (HCO-1230xa) to 2-chloro-3,3,3-trifluoro-1-propene (HFCO-1233xf);
   2,3,3,3-tetrachloro-1-propene (HCO-1230xf) to 2-chloro-3,3,3-trifluoro-1-propene (HFCO-1233xf);
   2-chloro-3,3,3-trifluoro-1-propene (HFCO-1233xf) to 2-chloro-1,1,1,2-tetrafluoropropane (HCFC-244bb);
   1,1,1,2,3-pentachloropropane (HCC-240db) to 2-chloro-1,1,1,2-tetrafluoropropane (HCFC-244bb);
   1,1,2,2,3-pentachloropropane (HCC-240aa) to 2-chloro-1,1,1,2-tetrafluoropropane (HCFC-244bb);
   2,3-dichloro-1,1,1-trifluoropropane (HCFC-243db) to 2-chloro-1,1,1,2-tetrafluoropropane (HCFC-244bb);
   1,1,2,3-tetrachloro-1-propene (HCO-1230xa) to 2-chloro-1,1,1,2-tetrafluoropropane (HCFC-244bb);

2,3,3,3-tetrachloro-1-propene (HCO-1230xf) to 2-chloro-1,1,1,2-tetrafluoropropane (HCFC-244bb);
1,1,1,2,3-pentachloropropane (HCC-240db) to 1,1,1,2,2-pentafluoropropane (HFC-245cb);
1,1,2,2,3-pentachloropropane (HCC-240aa) to 1,1,1,2,2-pentafluoropropane (HFC-245cb);
2,3-dichloro-1,1,1-trifluoropropane (HCFC-243db) to 1,1,1,2,2-pentafluoropropane (HFC-245cb);
1,1,2,3-tetrachloro-1-propene (HCO-1230xa) to 1,1,1,2,2-pentafluoropropane (HFC-245cb);
2,3,3,3-tetrachloro-1-propene (HCO-1230xf) to 1,1,1,2,2-pentafluoropropane (HFC-245cb).

12. Process according to claim 1, wherein the fluorination catalyst comprises chromium oxyfluoride, chromium oxides, chromium halides and mixtures thereof.

13. Process according to claim 1, wherein the fluorination catalyst contains one or more co-catalysts comprising a salt of a transition metal selected from the group consisting of Co, Zn, Mn, Mg, V, Mo, Te, Nb, Sb, Ta, Ni; or a phosphorous salt.

14. Process according to claim 1, comprising an activation step carried out before step (a) which comprises a first step of contacting the fluorination catalyst with a gas flow containing an oxidizing agent selected from oxygen, air, chlorine or a mixture of oxygen and nitrogen.

15. Process according to claim 14, wherein the activation step comprises a second step, subsequent to the first step, of treating the fluorination catalyst obtained after the first step with a gaseous mixture containing a reducing agent and an inert gas, said reducing agent being hydrogen or a $C_2$-$C_6$ hydrohalocarbon.

16. Process according to claim 1, wherein steps (a) and (b) are carried out alternately.

17. Process according to claim 1, wherein a purge of the reactor is carried out before and/or after step (b), the purge being carried out by introducing a stream of nitrogen in the reactor or by maintaining the reactor under vacuum.

* * * * *